US012630537B2

(12) United States Patent
McGowan et al.

(10) Patent No.: US 12,630,537 B2
(45) Date of Patent: *May 19, 2026

(54) PYRIDAZINONE AND METHODS OF USE THEREOF

(71) Applicant: ALIGOS THERAPEUTICS, INC., South San Francisco, CA (US)

(72) Inventors: David Craig McGowan, Brussels (BE); Pierre Jean-Marie Bernard Raboisson, Wavre (BE); Koen Vandyck, Beringen (BE); Jerome Deval, El Granada, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 453 days.

This patent is subject to a terminal disclaimer.

(21) Appl. No.: 18/144,004

(22) Filed: May 5, 2023

(65) Prior Publication Data

US 2024/0368128 A1 Nov. 7, 2024

Related U.S. Application Data

(63) Continuation of application No. PCT/US2021/058307, filed on Nov. 5, 2021.

(60) Provisional application No. 63/110,820, filed on Nov. 6, 2020.

(51) Int. Cl.

| | |
|---|---|
| ***C07D 403/12*** | (2006.01) |
| ***A61P 3/06*** | (2006.01) |
| ***A61P 5/14*** | (2006.01) |

(52) U.S. Cl.

CPC .............. *C07D 403/12* (2013.01); *A61P 3/06* (2018.01); *A61P 5/14* (2018.01); *C07B 2200/09* (2013.01)

(58) Field of Classification Search

CPC ....... C07D 403/12; C07D 211/06; A61P 3/06; A61P 5/14; A61P 5/00; A61P 9/00; A61P 35/00; A61P 43/00; A61P 1/16; A61P 3/04; A61P 3/10; C07B 2200/09; C07B 2200/07; A61K 31/53

See application file for complete search history.

(56) References Cited

U.S. PATENT DOCUMENTS 7,807,674 B2 * 10/2010 Haynes ..................... A61P 3/04 544/182

FOREIGN PATENT DOCUMENTS

WO WO-2019/240938 A1 12/2019
WO WO-2020/227549 A1 11/2020

OTHER PUBLICATIONS

Bookout et al., "Anatomical Profiling of Nuclear Receptor Expression Reveals a Hierarchical Transcriptional Network," Cell, Aug. 25, 2006, 126(4):789-799.

Chalasani et al., "The Diagnosis and Management of Non-alcoholic Fatty Liver Disease: Practice Guideline by the American Gastroenterological Association, American Association for the Study of Liver Diseases, and American College of Gastroenterology," Gastroenterology, 2012, 142(7):1592-1609.

Dulai et al., "Increased Risk of Mortality by Fibrosis Stage in Nonalcoholic Fatty Liver Disease: Systematic Review and Meta-Analysis," Hepatology, May 2017, 65(5):1557-1565.

Erion et al., "Targeting thyroid hormone receptor-B agonists to the liver reduces cholesterol and triglycerides and improves the therapeutic index," PNAS, Sep. 25, 2007, 104(39):15490-15495.

Flamant et al., "International Union of Pharmacology. LIX. The Pharmacology and Classification of the Nuclear Receptor Superfamily: Thyroid Hormone Receptors," Pharmacological Reviews, 2006, 58(4):705-711.

Haning et al., "Novel heterocyclic thryomimetics," Bioorganic & Medicinal Chemistry Letters, Apr. 1, 2005, 15(7):1835-1840.

Hartley et al., "A Thyroid Hormone-Based Strategy for Correcting the Biochemical Abnormality in X-Linked Adrenoleukodystrophy," Endocrinology, May 2017, 158(5):1328-1338.

Harvey et al., "Mechanism of Thyroid Hormone Action," Thyroid, Jun. 2002, 12(6):441-446.

Hirano et al., "Thyromimetics: a review of recent reports and patents (2004-2009)," Expert Opin. Ther. Pat., Feb. 2010, 20(2):213-228.

Kowalik et al., "Thyroid Hormones, Thyromimetics and Their Metabolites in the Treatment of Liver Disease," Frontiers in Endocrinology, Jul. 10, 2018, 9:382, 11 pages.

Lazo et al., "Nonalcoholic Fatty Liver disease (NAFLD): Is It Really a Serious Condition?", Hepatology, Oct. 2012, 56(4):1580-1584.

Milanesi et al., "Beam Me In: Thyroid Hormone Analog Targets Alternative Transporter in Mouse Model of X-Linked Adrenoleukodystrophy," Endocrinology, May 2017, 158:1116-1119.

Serfaty et al., "Definition and natural history of metabolic steatosis: clinical aspects of NAFLD, NASH and cirrhosis," Diabetes and Metabolism, 2008, 34:634-637.

Younossi et al., "Current and Future Therapeutic Regimens for Nonalcoholic Fatty Liver Disease and Nonalcoholic Steatohepatitis," Hepatology, Jul. 2018, 68(1):361-371.

Younossi et al., "Global Epidemiology of Nonalcoholic Fatty Liver Disease—Meta-Analytic Assessment of Prevalence, Incidence and Outcomes," Hepatology, Jul. 2016, 64(1):73-84.

* cited by examiner

*Primary Examiner* — Robert H Havlin
(74) *Attorney, Agent, or Firm* — Foley & Lardner LLP

(57) ABSTRACT

Disclosed herein are methods of modulating the activity of a thyroid hormone receptor beta and methods of treating disease using a pyridazinone compound.

2 Claims, No Drawings

PYRIDAZINONE AND METHODS OF USE THEREOF

CROSS-REFERENCE TO RELATED APPLICATIONS

This application is a continuation of International Patent Application No. PCT/US2021/058307, filed Nov. 5, 2021, which claims the benefit of priority to U.S. Provisional Patent Application Ser. No. 63/110,820, filed on Nov. 6, 2020, the entire disclosure of each of which is hereby incorporated by reference herein.

FIELD OF THE DISCLOSURE

The present disclosure is in the field of pharmaceutical compounds and preparations and method of their use in the treatment of disease. In particular, the present disclosure is in the field of THR-β modulators and their use.

BACKGROUND OF THE DISCLOSURE

In parallel with the global increase in obesity, nonalcoholic fatty liver disease (NAFLD) is becoming the leading cause of chronic liver disease and liver transplantation worldwide [1,2]. NAFLD is believed to affect 30% of the adult population and 70-80% of individuals who are obese and diabetic. NAFLD is defined as excess liver fat accumulation greater than 5% induced by causes other than alcohol intake. NAFLD progresses to liver inflammation (nonalcoholic steatohepatitis, NASH) and fibrosis in a variable proportion of individuals, ultimately leading to liver failure and hepatocellular carcinoma (HCC) in susceptible individuals [3].

In the United States alone, NASH is the third most common indication for liver transplantation and is on a trajectory to become the most common [4]. The most important medical need in patients with NAFLD and NASH is an effective treatment to halt the progression and possibly reverse fibrosis, which is the main predictor of liver disease evolution [5,6].

Thyroid hormone (TH) is essential for normal development, growth and metabolism of all vertebrates. Its effects are mediated principally through triiodothyronine (T3), which acts as a ligand for the TH receptors (TRs, or THRs) β1, β2 and α1 [7]. In the absence of ligand, TR first binds as a heterodimer or homodimer on TH response elements (TRE) located in the promoter regions of target genes, where it interacts with corepressors. Upon ligand binding, the TR homodimers are dissociated in favor of heterodimer formation with the retinoid-X receptor (RXR), resulting in release of the corepressors and recruitment of coactivators. This new complex attracts a large number of proteins which engage the RNA polymerase II in the transcription of the targeted genes.

Two different genetic loci, denoted THRA and THRB, are responsible for encoding multiple interrelated TR isoforms that have distinct tissue distributions and biological functions. The two major isoforms with the broadest level of tissue expression are TRα1 and TRβ1 [8]. While TRα1 is expressed first during fetal development and is widely expressed in adult tissues, TRβ1 appears later in development and displays highest expression in the adult liver, kidney, and lung [9]. TRα1 is a key regulator of cardiac output, whereas TRβ1 helps in the control of metabolism in the liver. Importantly, the natural thyroid hormone T3 activates both TRα1 and TRβ1 without any significant selectivity.

Design of thyromimetic small molecule agents led to the identification of TR (or THR) agonists with varying levels of TRβ selectivity despite high structural similarity between the ligand-binding domains for TRβ and TRα. TRβ selectivity achieved by some of these compounds resulted in an improved therapeutic index for lipid lowering relative to cardiac effects such as heart rate, cardiac hypertrophy, and contractility [10-12].

Another strategy to avoid activation of TRα in cardiac tissue is to design prodrugs of phosphonate-containing TR agonists that are specifically converted to the active agonist in the liver but remain stable as an inactive prodrug in blood and extrahepatic tissues, including the heart [13]. TRα and TRβ agonists are also used in indications other than liver-related disorders, as has been known in the art. For example, TRβ selective agonists may be useful in the treatment of X-linked adrenoleukodystrophy [14, 15].

SUMMARY

Provided herein, in one aspect, is an enantiomeric compound obtained through chromatography purification of a mixture consisting of

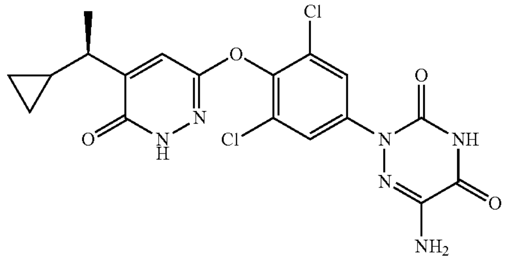 [SMILES: C[C@@H](c1cc(Oc2c(Cl)cc(-n3nc(N)c(=O)[nH]c3=O)cc2Cl)n[nH]c1=O)C1CC1]

and

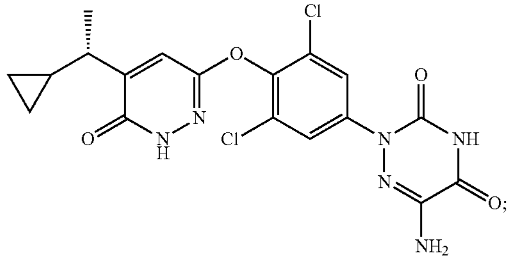

wherein the purification is performed using a 2 cm×25 cm column containing amylose tris-[(S)-α-methylbenzylcarbamate] coated on 5 μm silica gel, under conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm;

and the enantiomeric compound is eluted first under the conditions. In some embodiments, the enantiomeric compound has greater THR-β activity in a TR-FRET thyroid receptor beta coactivator assay or a HEK293T cell reporter assay than its enantiomeric counterpart which elutes second during the chromatography purification.

Provided herein, in another aspect, is a compound having a chemical structure of:

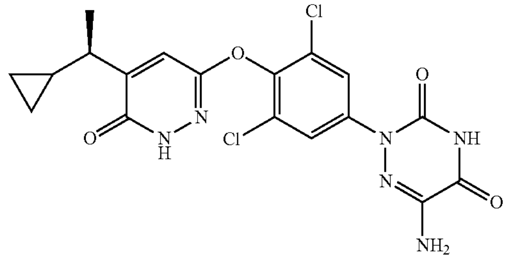

or a pharmaceutically acceptable salt thereof.

Provided herein, in another aspect, is a compound having a chemical structure of:

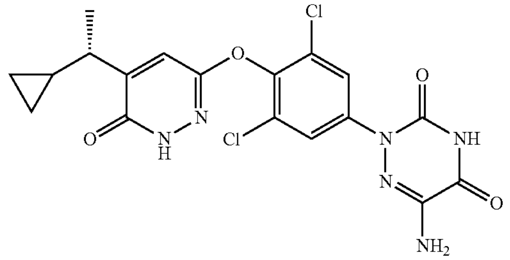 [SMILES: C[C@H](c1cc(Oc2c(Cl)cc(-n3nc(N)c(=O)[nH]c3=O)cc2Cl)n[nH]c1=O)C1CC1]

or a pharmaceutically acceptable salt thereof.

Provided herein, in another aspect, is a compound that has a retention time of about 20.8 minutes when determined using a 2 cm×25 cm column containing amylose tris-[(S)-α-methylbenzylcarbamate] coated on 5 μm silica gel, under conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm;

wherein the compound is an enantiomer of

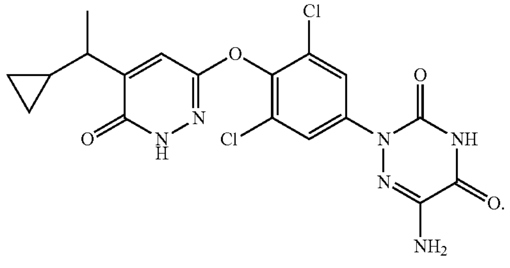

Provided herein, in another aspect, is a method of selectively increasing the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a blood plasma concentration in a rat of about 300-400 ng/mL at 12 hours after intravenous administration, wherein the compound is an enantiomer of

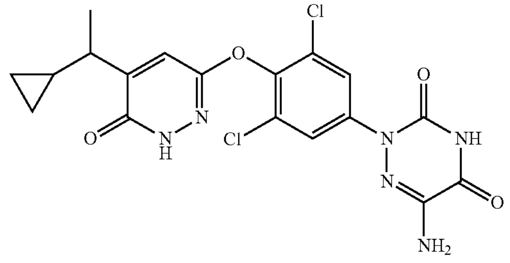

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

In some embodiments, the blood plasma concentration is about 336 ng/mL. In some embodiments, the compound has at least a 9-fold selectivity for thyroid hormone receptor beta over thyroid hormone receptor alpha in a TR-FRET thyroid receptor beta coactivator assay. In some embodiments, the compound has a half-life of over 360 minutes in a mouse, rat, or human hepatocyte assay. In some embodiments, the compound has greater THR-β activity in a TR-FRET thyroid receptor beta coactivator assay than its enantiomeric counterpart which elutes second under the chromatography conditions.

Provided herein, in another aspect, is a method of selectively increasing the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a half-life in a rat of about 5.25 hours after intravenous administration, and wherein the compound is an enantiomer of

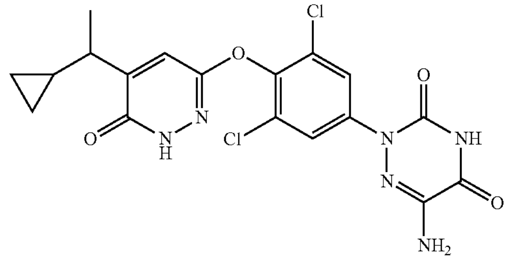 [SMILES: CC(c1cc(Oc2c(Cl)cc(-n3nc(N)c(=O)[nH]c3=O)cc2Cl)n[nH]c1=O)C1CC1]

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

In some embodiments, the compound has at least a 9-fold selectivity for thyroid hormone receptor beta over thyroid hormone receptor alpha in a TR-FRET thyroid receptor beta coactivator assay. In some embodiments, the compound has a half-life of over 360 minutes in a mouse, rat, or human hepatocyte assay. In some embodiments, the compound has greater THR-β activity in a TR-FRET thyroid receptor beta coactivator assay than its enantiomeric counterpart which elutes second under the chromatography conditions.

Provided herein, in another aspect, is a method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a blood plasma concentration in a rat of about 300-400 ng/mL at 12 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer, and wherein the compound is an enantiomer of

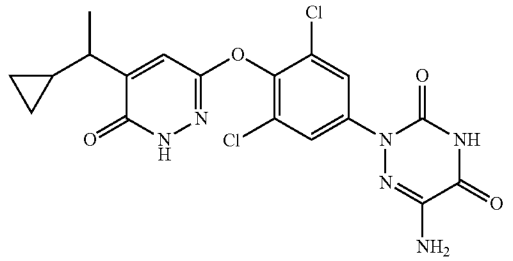 [SMILES: CC(c1cc(Oc2c(Cl)cc(-n3nc(N)c(=O)[nH]c3=O)cc2Cl)n[nH]c1=O)C1CC1]

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

In some embodiments, the blood plasma concentration is about 336 ng/mL. In some embodiments, the compound has at least a 9-fold selectivity for thyroid hormone receptor beta over thyroid hormone receptor alpha in a TR-FRET thyroid receptor beta coactivator assay. In some embodiments, the compound has a half-life of over 360 minutes in a mouse, rat, or human hepatocyte assay. In some embodiments, the compound has greater THR-β activity in a TR-FRET thyroid receptor beta coactivator assay than its enantiomeric counterpart which elutes second under the chromatography conditions.

Provided herein, in another aspect, is a method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a half-life in a rat of about 5.25 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer, and wherein the compound is an enantiomer of

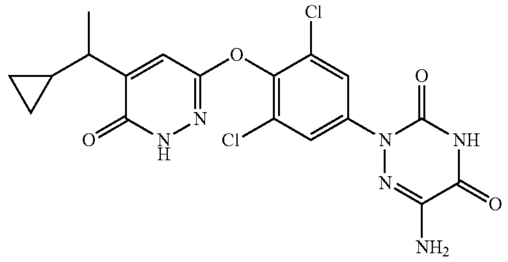

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

In some embodiments, the compound has at least a 9-fold selectivity for thyroid hormone receptor beta over thyroid hormone receptor alpha in a TR-FRET thyroid receptor beta coactivator assay. In some embodiments, the compound has a half-life of over 360 minutes in a mouse, rat, or human hepatocyte assay. In some embodiments, the compound has greater THR-β activity in a TR-FRET thyroid receptor beta coactivator assay than its enantiomeric counterpart which elutes second under the chromatography conditions.

Provided herein, in another aspect, is a method of selectively modulating the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a blood plasma concentration in a rat of about 336 ng/mL at 12 hours after intravenous administration. In some embodiments, the compound has at least a 9-fold selectivity for thyroid hormone receptor beta over thyroid hormone receptor alpha. In some embodiments, the compound has a half-life of over 360 minutes in a mouse, rat, or human hepatocyte assay. In some embodiments, the compound is compound 1a (as defined in example 1).

Provided herein, in another aspect, is a method of selectively modulating the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a half-life in a rat of about 5.25 hours after intravenous administration. In some embodiments, the compound has at least a 9-fold selectivity for thyroid hormone receptor beta over thyroid hormone receptor alpha. In some embodiments, the compound has a half-life of over 360 minutes in a mouse, rat, or human hepatocyte assay. In some embodiments, the compound is compound 1a.

Provided herein, in another aspect, is a method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a blood plasma concentration in a rat of about 336 ng/mL at 12 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer. In some embodiments, the compound has at least a 9-fold selectivity for thyroid hormone receptor beta over thyroid hormone receptor alpha. In some embodiments, the compound has a half-life of over 360 minutes in a mouse, rat, or human hepatocyte assay. In some embodiments, the compound is compound 1a.

Provided herein, in another aspect, is a method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a half-life in a rat of about 5.25 hours after intravenous administration, and wherein the disorder or disease is selected non-alcoholic from steatohepatitis (NASH), obesity, hyperlipidemia, hypercholesterolemia, diabetes, liver steatosis, atherosclerosis, cardiovascular diseases, hypothyroidism, and thyroid cancer. In some embodiments, the compound has at least a 9-fold selectivity for thyroid hormone receptor beta over thyroid hormone receptor alpha. In some embodiments, the compound has a half-life of over 360 minutes in a mouse, rat, or human hepatocyte assay. In some embodiments, the compound is compound 1a.

DETAILED DESCRIPTION

Definitions

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, the abbreviations "TR" and "THR" refer to thyroid hormone receptors.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methane-sulfonates, ethanesulfonates, p-toluenesulfonates and salicylates.

As used herein, "pharmaceutically acceptable ester" refers to an ester of a compound that does not cause significant irritation to a patient to which it is administered. The ester is metabolized in the body to result in the parent compound, e.g., the claimed compound. Accordingly, the ester does not abrogate the biological activity and properties of the compound. Pharmaceutical esters can be obtained by reaction of a compound disclosed herein with an alcohol. Methyl, ethyl, and isopropyl esters are some of the common esters to be prepared. Other esters suitable are well-known to those skilled in the art (see, for example Wuts, P. G. M., Greene's Protective Groups in Organic Synthesis, $5^{th}$ Ed., John Wiley & Sons, New York, N.Y., 2014, which is incorporated herein by reference in its entirety).

Where the processes for the preparation of the compounds disclosed herein give rise to mixtures of stereoisomers, such isomers may be separated by conventional techniques such as preparative chiral chromatography. The preparative chiral chromatography may be performed using columns containing chiral stationary phases, such as, but not limited to, polysaccharide-based, protein-based, helical polymer-based or macrocyclic stationary phases. Other chiral columns include ligand exchange columns and pirkle-type columns. Commercially available chiral columns include, but are not limited to, CHIRALPAK® AS-H, CHIRALPAK® IG, CHIRALPAK® IC, CHIRALPAK® IC-3, CHIRALPAK® IA, CHIRALPAK® IA-3, LUX amylose-1, and Reflect C-Amylose A columns, The compounds disclosed herein may be isolated on certain chiral column(s) that reverse the order of elution compared to other chiral column(s). Nevertheless, the isolated compounds can be identified by their biological activity.

The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved by formation of diastereomeric esters or amides followed by chromatographic separation and removal of the chiral auxiliary.

It is understood that, in any compound of the presently disclosed compounds having one or more chiral centers, if an absolute stereochemistry is not expressly indicated, then each center may independently be R or S or a mixture thereof. In addition, it is understood that, in any compound of the presently disclosed compounds having one or more double bond(s) generating geometrical isomers that can be defined as E or Z each double bond may independently be E or Z, or a mixture thereof.

It is understood that the disclosure of a compound herein inherently includes the disclosure of a tautomer thereof, if applicable. For instance, the disclosure of:

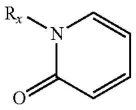

(wherein $R_x$ is H)
also includes the disclosure of:

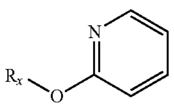

and vice versa, even if only one of the two structures is disclosed.

Throughout the present disclosure, when a compound is illustrated or named, it is understood that the isotopically enriched analogs of the compound are also contemplated. For example, a compound may have a deuterium incorporated instead of a hydrogen, or a carbon-13 instead of carbon with natural isotopic distribution. The isotopic enrichment may be in one location on the compound, i.e., only one hydrogen is replaced by a deuterium, or in more than one location. The present disclosure also encompasses compounds where all the similar atoms are replaced by their less common isotope, for example, a perdeutero compound where all the hydrogen atoms are replaced by a deuterium. The isotopically enriched compounds are useful when obtaining NMR spectra or when making use of an isotope effect in managing the kinetics of the reaction the compound undergoing.

The term "pharmaceutical composition" refers to a mixture of one or more compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "pharmaceutically acceptable" defines a carrier or diluent that does not abrogate the biological activity and properties of the compound.

Compounds

In one aspect, disclosed herein are enantiomers of compound 1:

(compound 1)

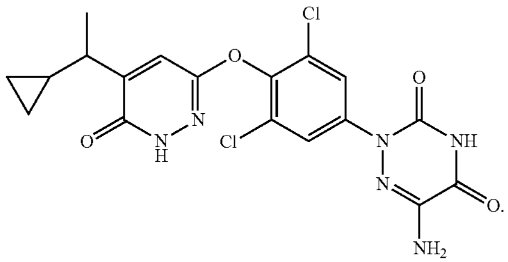

The preparation of compound 1 is described in the Examples below. The enantiomers of compound 1 may be separated using methods known in the art. More particularly, the first eluting compound (at a retention time of 20.83 min) under the following preparative HPLC conditions: Column, CHIRALPAK AS-H, 2.0 cm×25 cm (5 μm); Mobile Phase A: $CO_2$, Mobile Phase B: $CH_3OH$ (0.1% 2M $NH_3$—$CH_3OH$); Flow rate: 45 mL/min; Gradient: 20% B; Detection wavelength: 220 nm; is referred herein as compound 1a, whereas the second eluting compound (at a retention time of 22.78 min) is referred herein as compound 1b.

Pharmaceutical Compositions

In another aspect, disclosed herein are pharmaceutical compositions comprising, consisting essentially of, or consisting of compound 1a as described herein and at least one pharmaceutically acceptable excipient.

The pharmaceutical composition disclosed herein may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition disclosed herein may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, transdermal, rectal, transmucosal, or intestinal administration; parenteral delivery, including intramuscular, subcutaneous, intravenous, intramedullary injections, as well as inhalation, intrathecal, direct intraventricular, intraperitoneal, intranasal, or intraocular injections.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. These pharmaceutical compositions, then, may be formulated in a conventional manner using one or more known physiologically acceptable carriers comprising excipients and/or auxiliaries, which facilitate processing of the active compounds into preparations that can be used pharmaceutically. Any of the well-known techniques, carriers, and excipients may be used as suitable and as understood in the art; e.g., in Remington's Pharmaceutical Sciences, above.

Pharmaceutical compositions suitable for use in the presently disclosed formulations include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. In some embodiments, a therapeutically effective amount means an amount of compound effective to alleviate or ameliorate symptoms of disease or prolong the survival of the subject being treated.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example 1 to 200 mg or each active ingredient of the pharmaceutical compositions disclosed herein or a pharmaceutically acceptable salt thereof calculated as the free base or free acid, the composition being administered 1 to 4 times per day or per week. Alternatively, the compositions disclosed herein may be administered by continuous such as sustained, delayed, or extended release, preferably at a dose of each ingredient up to 500 mg per day. Thus, the total daily dosage by oral administration of each ingredient will typically be in the range 0.1 mg to 2000 mg.

Methods of Treatment

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a composition comprising, consisting essentially of, or consisting of a compound, or a tautomer thereof, or a pharmaceutically acceptable salt thereof, wherein the composition provides a blood plasma concentration in a rat of about 336 ng/mL at 12 hours after intravenous administration. In some embodiments, the compound is compound 1a.

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a composition comprising, consisting essentially of, or consisting of a compound, or a tautomer thereof, or a pharmaceutically acceptable salt thereof, wherein the composition provides a half-life in a rat of about 5.25 hours after intravenous administration. In some embodiments, the compound is compound 1a.

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a composition comprising, consisting essentially of, or consisting of compound 1a as described herein.

In some embodiments, a health care professional, such as a physician, physician's assistant, nurse practitioner, or the like, identifies an individual as being in need of treatment for the thyroid hormone receptor related disorder, and/or a candidate for treatment with a compound disclosed herein. The identification may be based on medical test results, non-responsiveness to other, first-line therapies, the specific nature of the particular liver disorder, or the like.

In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a blood plasma concentration in a rat of about 336 ng/mL at 12 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer. In some embodiments, the compound is compound 1a.

In another aspect, disclosed herein are methods of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a half-life in a rat of about 5.25 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer. In some embodiments, the compound is compound 1a.

In another aspect, disclosed herein are methods of treating a disorder or disease in a subject in need thereof, the method comprising, consisting essentially of, or consisting of administering to the subject a therapeutically effective amount of a composition comprising, consisting essentially of, or consisting of compound 1a as described herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating NASH in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a blood plasma concentration in a rat of about 336 ng/mL at 12 hours after intravenous administration. In some embodiments, the compound is compound 1a.

In another aspect, disclosed herein are methods of treating NASH in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a half-life in a rat of about 5.25 hours after intravenous administration. In some embodiments, the compound is compound 1a.

In another aspect, disclosed herein are methods of treating NASH in a subject in need thereof, the method comprising, consisting essentially of, or consisting of administering to the subject a therapeutically effective amount of a composition comprising, consisting essentially of, or consisting of compound 1a as described herein.

In another aspect, disclosed herein are methods of treating obesity in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a blood plasma concentration in a rat of about 336 ng/mL at 12 hours after intravenous administration. In some embodiments, the compound is compound 1a.

In another aspect, disclosed herein are methods of treating obesity in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a half-life in a rat of about 5.25 hours after intravenous administration. In some embodiments, the compound is compound 1a.

In another aspect, disclosed herein are methods of treating obesity in a subject in need thereof, the method comprising, consisting essentially of, or consisting of administering to the subject a therapeutically effective amount of a composition comprising, consisting essentially of, or consisting of compound 1a as described herein.

In another aspect, disclosed herein are methods of treating hyperlipidemia in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a blood plasma concentration in a rat of about 336 ng/mL at 12 hours after intravenous administration. In some embodiments, the compound is compound 1a.

In another aspect, disclosed herein are methods of treating hyperlipidemia in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a half-life in a rat of about 5.25 hours after intravenous administration. In some embodiments, the compound is compound 1a.

In another aspect, disclosed herein are methods of treating hyperlipidemia in a subject in need thereof, the method comprising, consisting essentially of, or consisting of administering to the subject a therapeutically effective amount of a composition comprising, consisting essentially of, or consisting of compound 1a as described herein.

In another aspect, disclosed herein are methods of treating hypercholesterolemia in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a blood plasma concentration in a rat of about 336 ng/mL at 12 hours after intravenous administration. In some embodiments, the compound is compound 1a.

In another aspect, disclosed herein are methods of treating hypercholesterolemia in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a half-life in a rat of about 5.25 hours after intravenous administration. In some embodiments, the compound is compound 1a.

In another aspect, disclosed herein are methods of treating hypercholesterolemia in a subject in need thereof, the method comprising, consisting essentially of, or consisting of administering to the subject a therapeutically effective amount of a composition comprising, consisting essentially of, or consisting of compound 1a as described herein.

In another aspect, disclosed herein are methods of treating diabetes in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a blood plasma concentration in a rat of about 336 ng/mL at 12 hours after intravenous administration. In some embodiments, the compound is compound 1a.

In another aspect, disclosed herein are methods of treating diabetes in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a half-life in a rat of about 5.25 hours after intravenous administration. In some embodiments, the compound is compound 1a.

In another aspect, disclosed herein are methods of treating diabetes in a subject in need thereof, the method comprising, consisting essentially of, or consisting of administering to the subject a therapeutically effective amount of a composition comprising, consisting essentially of, or consisting of compound 1a as described herein.

In another aspect, disclosed herein are methods of treating liver steatosis in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a blood plasma concentration in a rat of about 336 ng/mL at 12 hours after intravenous administration. In some embodiments, the compound is compound 1a.

In another aspect, disclosed herein are methods of treating liver steatosis in a subject in need thereof, the method comprising, consisting essentially of, or consisting of administering to the subject a therapeutically effective amount of a composition comprising, consisting essentially of, or consisting of a compound, or a tautomer thereof, or a pharmaceutically acceptable salt thereof, wherein the composition provides a half-life in a rat of about 5.25 hours after intravenous administration. In some embodiments, the compound is compound 1a.

In another aspect, disclosed herein are methods of treating liver steatosis in a subject in need thereof, the method comprising, consisting essentially of, or consisting of administering to the subject a therapeutically effective amount of a composition comprising, consisting essentially of, or consisting of compound 1a as described herein.

In another aspect, disclosed herein are methods of selectively modulating the activity of a thyroid hormone receptor beta (THR-β) comprising, consisting essentially of, or consisting of contacting a composition comprising, consisting essentially of, or consisting of a compound, or a tautomer thereof, or a pharmaceutically acceptable salt thereof, with the thyroid hormone receptor, wherein the composition provides a blood plasma concentration in a rat of about 336 ng/mL at 12 hours after intravenous administration. In some embodiments, the compound is compound 1a. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a composition comprising, consisting essentially of, or consisting of a compound, or a tautomer thereof, or a pharmaceutically acceptable salt thereof, with the thyroid hormone receptor, wherein the composition provides a half-life in a rat of about 5.25 hours after intravenous administration. In some embodiments, the compound is compound 1a. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a composition comprising, consisting essentially of, or consisting of compound 1a as described herein, with the thyroid hormone receptor. In some embodiments, the contacting is in vitro or ex vivo, whereas in other embodiments, the contacting is in vivo.

EXAMPLES

Example 1. Preparation of Compounds 1a and 1b 1a or 1b

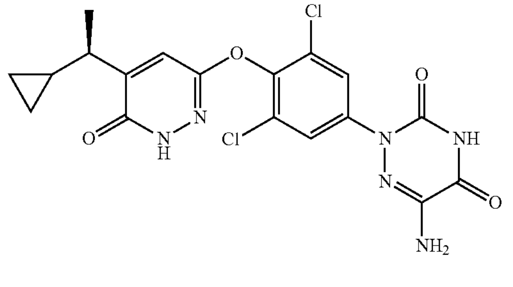

-continued 1a or 1b

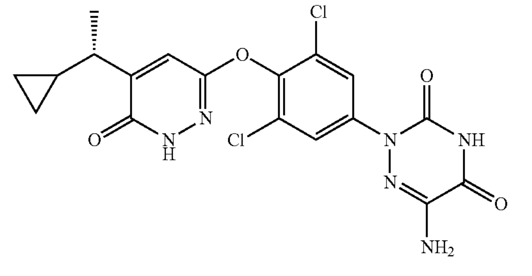

A solution of 4-toluenesulfonyl hydrazide (20.0 g, 107 mmol) in $CH_3OH$ (200 mL) was stirred and heated to 60° C. until the 4-toluenesulfonyl hydrazide (20.0 g, 107 mmol) was dissolved. Then cyclopropyl methyl ketone (10.8 g, 129 mmol) was added to the mixture slowly. The resulting solution was stirred at 60° C. for 1 h. The resulting solution was concentrated under reduced pressure. The residue was chromatographed on a silica gel column with petroleum ether/ethyl acetate (4/1) to provide N'-(1-cyclopropylethylidene)-4-methylbenzenesulfonohydrazide (18 g, 66%) as a white solid. $^1H$ NMR (400 MHz, DMSO-$d_6$) δ 9.86 (s, 1H), 7.65-7.72 (m, 2H), 7.36-7.39 (m, 2H), 2.36 (s, 3H), 1.57 (s, 3H), 1.44-1.50 (m, 1H), 0.61-0.64 (m, 2H), 0.50-0.59 (m, 2H). LC-MS (ESI, m/z): 253 $[M+H]^+$.

To a stirred solution of N'-(1-cyclopropylethylidene)-4-methylbenzenesulfonohydrazide (9.00 g, 35.7 mmol), lithium t-butoxide (5.71 g, 71.3 mmol), CuI (2.04 g, 10.7 mmol) in dioxane (20 mL) under $N_2$ atmosphere was added ethynyltriisopropylsilane (4.55 g, 25.0 mmol). The reaction mixture was stirred at 110° C. for 1 h. The reaction mixture was filtered through celite pad and celite pad was washed with THF (3×50 mL). The filtrate was collected and concentrated under reduced pressure. The residue was chromatographed on a silica gel column with petroleum ether to provide (3-cyclopropylbut-1-yn-1-yl)triisopropylsilane (5 g, 56%) as a brown oil. $^1H$ NMR (400 MHz, DMSO-$d_6$) δ 2.51-2.54 (m, 1H), 1.16 (d, J=4.0 Hz, 3H), 0.90-1.01 (m, 19H), 0.80-0.85 (m, 3H), 0.32-0.39 (m, 2H), 0.23-0.29 (m, 2H).

To a solution of (3-cyclopropylbut-1-yn-1-yl)triisopropylsilane (5 g, 20.0 mmol) in THF (10 mL) was added tetrabutylammonium fluoride (30 mL, 1M in THF, 30.0 mmol). The reaction mixture was stirred at room temperature for 3 h, then distilled at 80° C. to afford but-3-yn-2-ylcyclopropane (28 mL, in THF solution). GC-MS (ESI, m/z): 94 $[M]^+$.

A solution of dichloro-1,2,4,5-tetrazine (1.20 g, 7.95 mmol) and but-3-yn-2-ylcyclopropane (2.00 g, 21.2 mmol) in dioxane (24 mL) was stirred overnight at 100° C. The reaction mixture was separated by prep HPLC Column: XBridge Prep OBD C18, 19×250 mm, 5 μm; mobile Phase A: Water (0.05% TFA), mobile Phase B: $CH_3CN$; flow rate: 25 mL/min; Gradient: 53% B to 71% B in 8 min; 254 nm) to afford 3,6-dichloro-4-(1-cyclopropylethyl)pyridazine (600 mg, 35%) as a white solid. $^1H$ NMR (400 MHz, $CDCl_3$) δ 7.55 (s, 1H), 2.38-2.45 (m, 1H), 1.33 (d, J=8.0 Hz, 3H), 0.93-1.03 (m, 1H), 0.67-0.74 (m, 1H), 0.51-0.58 (m, 1H), 0.31-0.37 (m, 1H), 0.13-0.20 (m, 1H). LC-MS (ESI, m/z): 217 $[M+H]^+$.

A solution of 3,6-dichloro-4-(1-cyclopropylethyl) pyridazine (600 mg, 2.76 mmol), t-butyl N-[2-(3,5-dichloro-4-hydroxyphenyl)-3,5-dioxo-4H-1,2,4-triazin-6-yl]carbamate (2.15 g, 5.53 mmol), $K_2CO_3$ (1.15 g, 8.29 mmol) and CuI (263 mg, 1.38 mmol) in DMSO (20 mL) was stirred overnight at 110° C., and then quenched with water (20 mL). The resulting mixture was extracted with ethyl acetate (3×20 mL). The combined organic layers were washed with brine (40 mL), dried over anhydrous sodium sulfate, the solids were removed by filtration and the filtrate was concentrated under reduced pressure. The crude product was chromatographed on a silica gel column with methanol/dichloromethane (1/9) to provide 6-amino-2-(3,5-dichloro-4-[[6-chloro-5-(1-cyclopropylethyl)pyridazin-3-yl]oxy]phenyl)-4H-1,2,4-triazine-3,5-dione (700 mg, 54%) as brown solid. LC-MS (ESI, m/z): 469 $[M+H]^+$.

To a solution of 6-amino-2-(3,5-dichloro-4-[[6-chloro-5-(1-cyclopropylethyl) pyridazin-3-yl]oxy]phenyl)-4H-1,2,4-triazine-3,5-dione (700 mg, 1.49 mmol) in acetic acid (10 mL) was added sodium acetate (611 mg, 7.45 mmol). The mixture was stirred overnight at 100° C. The mixture reaction was cooled to room temperature and quenched with water (20 mL) and stirred for 10 min. The resulting solid was isolated by filtration, washed with water (2×50 mL) petroleum ether (2×50 mL), then dried under reduced pressure to afford the crude product (300 mg), further purified by a C18 column with $CH_3CN/H_2O$ (4/6) to afford 6-amino-2-(3,5-dichloro-4-[[5-(1-cyclopropylethyl)-6-oxo-1H-pyridazin-3-yl]oxy] phenyl)-4H-1,2,4-triazine-3,5-dione (170 mg, 25%) as a yellow solid. LC-MS (ESI, m/z): 451 $[M+H]^+$.

The sample (160 mg) was separated by prep-chiral chromatography (Column: CHIRALPAK® AS-H, 2.0 cm×25 cm (5 μm); mobile phase A: $CO_2$, mobile phase B: $CH_3OH$ (0.1% 2M $NH_3$—$CH_3OH$)); flow rate: 45 mL/min; gradient: 20% B; 220 nm; Retention time (Rt) peak 1: 20.83 min; Rt peak 2: 22.78 min; injection volume: 4.8 mL; 17 runs) to provide the two isomers. CHIRALPAK® AS-H, 2.0 cm×25 cm (5 μm) is a polysaccharide-based chiral column containing amylose tris-[(S)-α-methylbenzylcarbamate] coated on 5 μm silica gel.

1st eluting isomer (compound 1a): 60 mg (95% pure) was purified by prep HPLC Column: Kinetex EVO C18, 30×150 mm, 5 μm; mobile Phase A: water (10 mmol/L $NH_4HCO_3$+0.1% $NH_3 \cdot H_2O$), mobile Phase B: $CH_3CN$; flow rate: 60 mL/min; gradient: 20% B to 40% B in 7 min; 254 nm) to provide a white solid (16.3 mg, 10%). $^1H$ NMR (400 MHz, DMSO-$d_6$) δ 12.20-12.30 (m, 2H), 7.86 (s, 2H), 7.56 (s, 1H), 6.65 (s, 2H), 2.11-2.29 (m, 1H), 1.25 (d, J=7.0 Hz, 3H), 1.03-1.12 (m, 1H), 0.41-0.62 (m, 2H), 0.12-0.30 (m, 2H). LC-MS (ESI, m/z): 451 $[M+H]^+$.

2nd eluting isomer (compound 1b): 40 mg (95% pure) was purified by prep HPLC Column: Kinetex EVO C18, 30×150 mm, 5 μm; mobile Phase A: water (10 mmol/L $NH_4HCO_3$+0.1% $NH_3 \cdot H_2O$), mobile Phase B: ACN; flow rate: 60 mL/min; Gradient: 20% B to 40% B in 7 min; 254 nm) to provide a white solid (4.8 mg, 3%). $^1H$ NMR (400 MHz, DMSO-$d_6$) δ 12.20 (br, 2H), 7.86 (s, 2H), 7.56 (s, 1H), 6.50 (s, 2H), 2.19-2.23 (m, 1H), 1.24 (d, J=7.0 Hz, 3H), 1.08-1.11 (m, 1H), 0.44-0.54 (m, 2H), 0.13-0.26 (m, 2H). LC-MS (ESI, m/z): 451 $[M+H]^+$.

Example 2. Biological Characterization of Compound 1a

THR Biochemical Assay

The TR-FRET thyroid receptor beta coactivator assay was used with slight, optimized modifications of the manufacturer's protocol (Invitrogen). The assay uses a terbium-labeled anti-GST antibody, a glutathione-S-transferase (GST) tagged human thyroid receptor, beta or alpha, ligand-binding domain (LBD), and a fluorescein labeled SRC2-2 coactivator peptide. The antibody interacts with the LBD, where the agonist also binds, resulting in increased affinity for the SRC2-2 coactivator peptide causing energy transfer of the acceptor fluorophore and a FRET emission shift from 495 to 520 nm. The energy transfer was detected as an increase in the fluorescence emission of the fluorescein acceptor, and a decrease in the fluorescence emission of the terbium donor. The assay was performed in a 384-well black plate in a final volume of 20 μL. Serial dilution of various test agonists was performed in DMSO (1% final DMSO concentration) and added to the test plate. Thyroid receptor beta LBD was added to the plate at a final concentration of 1 nM, followed by the mixture of the fluorescein labeled SRC2-2 coactivator peptide, and the terbium-labeled anti-GST antibody at final concentrations of 200 nM and 2 nM respectively. The assay was incubated for 1 hr at rt protected from light. The TR-FRET was then measured on a Victor multilabel reader (Perkin Elmer) using an excitation wavelength of 340 nm with emission filters of 495 nm and 520 nm. The assay was quantified by expressing a ratio (520:495) of the intensities, and the resulting activation curves; $EC_{50}$ values were generated using a sigmoidal dose response (variable slope) equation in GraphPad™ Prism 8.0. Data for compounds 1a and 1b and reference compound 2 are shown in Table 1.

HEK293T Reporter THRalpha/beta/RXR Reporter Assay

The purpose of this assay is to evaluate the effect of compounds on the thyroid hormone nuclear receptor pathway in HEK293T cells. To this end, HEK293T cells are transiently transfected with a luciferase reporter under the control of the thyroid response element (TRE), an RXR expression plasmid and either a THR alpha or THR beta expression plasmid. Transfected cells are stimulated with test compounds for 18-24 hours before activation of the thyroid hormone pathway is measured via a luciferase read-out.

Procedure. 24 hours prior to transfection, approximately 7×105 HEK293T (ATCC, catalog #CRL-3216) were plated in one well of a 6-well-plate using DMEM (Hyclone, catalog #SH30022) supplemented with 10% FBS (Gibco, catalog #16000-044) and incubated overnight. Transfection complexes were prepared by mixing 12 μL of Lipofectamine 2000 (Invitrogen catalog #11668019) with 4 μg of a plasmid mixture at a ratio of 1:1:4 (TRalpha or TRbeta:RXR:TRE-Luc) in 200 μL OptiMem (Invitrogen catalog #11058-021) and added to the cells. After overnight incubation, transfected cells were re-seeded at (1×104 cells/well, 30 μL/well) in a 384 microplate and incubated for an additional 5-6 hours. Ten five-fold dilutions of test compounds were prepared in DMSO and 30 nL was dispensed to the cells. Pure DMSO served as negative control while T3 (MCE catalog #HY-A0070) and GC-1 (MCE catalog #HY-14823) was used as positive controls. Approximately 18-24 h after compound addition, 384 well plates were allowed to adjust to rt, 30 μL One-Glo (Promega catalog #E6120) is added to each well and luminescence was measured on a Perkin Elmer Enspire plate reader. Percent agonism was calculated using the following equation: 100×(sample−negative control)/(positive control−negative control).

Microsomal Stability Assay Procedure

The assay was carried out in 96-well microtiter plates. Test compounds, at a final concentration of 1 μM was incubated at 37° C. with 0.5 mg/mL liver microsomes, and +/−1 mM NADPH in 100 mM potassium phosphate, pH 7.4 buffer with 3.3 mM $MgCl_2$. Each reaction mixture had a volume of 25 μL with a final DMSO of 0.1%. At each of the time points (0, 15, 30 and 60 min), incubation was stopped by adding 150 μL of the quenching solutions (100% acetonitrile, 0.1% formic acid) and subsequently the mixtures were vortexed vigorously for 20 min and centrifuged at 4,000 RPM at 4° C. The supernatants (80 μL) were transferred to a clean 96-well plate and analyzed by LC/MS/MS. Verapamil at 1 μM with a final 0.1% DMSO was included as a positive control to verify assay performance. Data for compound 1a and reference compound 2 are shown in Table 1.

Reference compound 2 corresponds to a compound of the chemical structure:

(compound 2)

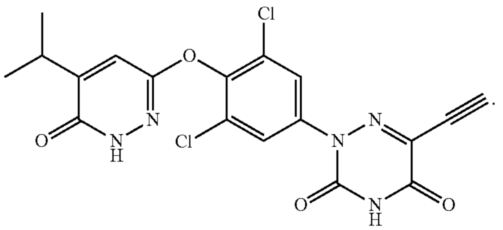

Compound 2 has been previously disclosed in WO 2019240938.

Hepatocyte Stability Assay Procedure

Cryopreserved hepatocytes were taken from the liquid nitrogen tank and thawed quickly in a 37° C. water bath. As soon as the cells pulled away from the vial wall, they were decanted into 48 mL of warm thawing (HT) medium. Cells were centrifuged for 5 minutes at 420 RPM (50 g). After removing the supernatant, the pellets were re-suspended in 4 mL of warm Dulbecco's Modified Eagle Medium (DMEM). Cell density was counted by a hemocytometer.

The assay was carried out in 96-well microtiter plates. The study compound was incubated at 1 μM with 0.5 million cells/mL hepatocytes in DMEM for 0, 60, 120, and 180 minutes at 37° C. The volume of the incubation mixture was 37 μL with a final DMSO content of 0.1%. At each time point, the incubation was stopped by the addition of 150 μL quenching solution (100% acetonitrile, 0.1% formic acid containing the internal standard bucetin at 15 nM). Subsequently, the mixtures were vortexed for 20 minutes and centrifuged at 4,000 RPM at 10° C. An aliquot of 80 μL of the supernatant was transferred to a clean 96-well plate and analyzed by LC/MS/MS. Midazolam at 1 μM with a final DMSO content of 0.1% was included as a positive control to verify the assay performance. Data for compound 1a and reference compound 2 are shown in Table 1.

Pharmacokinetics in Rat

Male Sprague-Dawley rats were administered the study compound as an i.v. bolus dose of 1 mg/kg in a 0.500 mg/mL solution in 60% PEG400 in water. Data for compound 1a and reference compound 2 are shown in Table 1.

TABLE 1

| | Compound | | |
|---|---|---|---|
| | 1a | 1b | 2 |
| Biochemical Activity | | | |
| $EC_{50}$ THR-α (nM) | 252 | 399 | 73 |
| $EC_{50}$ THR-β (nM) | 26 | 63 | 14 |
| THR-β Selectivity | 9.5 (n = 3) | 6 (n = 3) | 5 (n = 2) |
| HEK 293 Activity | | | |
| $EC_{50}$ THR-α (nM) | 201 | 715 | 319 |
| $EC_{50}$ THR-β (nM) | 38 | 110 | 60 |
| THR-β Selectivity | 5 (n = 3) | 6.5 (n = 3) | 4 (n = 2) |
| Pharmacokinetics | | | |
| iv dose (mg/kg) | 1 | — | 1 |
| Vehicle: 0.500 mg/mL in 60% PEG400 in water, clear solution | | | |
| $T_{1/2}$ (h) | 5.25 | — | 1.31 |
| Cl (mL/min/kg) | 2.14 | — | 9.14 |
| Plasma conc. 12 h (ng/mL) | 336 | — | NA* |
| Liver conc. 12 h (ng/g) | 14367 | — | NA* |
| Liver Microsomes $T_{1/2}$ in minutes (% Remaining) | | | |
| mouse | >60 (100) | >60 (92) | >60 (94) |
| rat | >60 (98) | >60 (91) | >60 (85) |
| human | >60 (107) | >60 (93) | >60 (84) |
| Hepatocytes $T_{1/2}$ in minutes (% Remaining) | | | |
| mouse | >360 (88) | >360 (101) | 71 (18) |
| rat | >360 (107) | >360 (106) | 86 (24) |
| human | >360 (100) | >360 (86) | 103 (31) |

*BQL (below quantification limit) at 24 h, NA = not available

Compound 1a shows higher in vitro THR-β selectivity compared to its enantiomer, compound 1b in the biochemical assay. Compound 1a has an unexpectedly longer in vivo half-life compared to compound 2. The in vitro metabolic stability of compound 1a is higher than compound 2 with respect to liver microsomal or whole cell hepatocyte data. The in vitro metabolic stability of compound 1a is higher than enantiomer, compound 1b with respect to liver microsomal data, as well as higher stability in whole cell human hepatocytes.

TABLE 2

| Compound 1a Pharmacokinetic Profile | | |
|---|---|---|
| | Mouse | Rat |
| CL (mL/min/kg) | 6.30 | 2.14 |
| $T_{1/2}$ (h) | 2.87 | 5.25 |
| Liver/Heart Concentration | 27.6 at 24 h | 62 at 12 h |

Cholesterol Reduction in a Murine Efficacy Model

Model description. WT C57BL/6 mice were fed a high fat diet (D12109C) for 2 weeks. Prior to the administration of compound 1a, blood was drawn to measure the baseline lipid levels. Compound 1a was dosed daily (p.o.) for 7 days. Blood was drawn to measure lipid levels.

Compound 1a demonstrated a 24.5% reduction in cholesterol at a daily, oral dose of 0.025 mg/kg BID.

REFERENCES

1. Younossi, Z M, Koenig, A B, Abdelatif, D, Fazel, Y, Henry, L, Wymer, M. Global epidemiology of nonalcoholic fatty liver disease-Meta-analytic assessment of prevalence, incidence, and outcomes. Hepatology, 2016, 64(1):73e84.
2. Gastroenterology. 2012 June; 142(7): 1592-609. doi: 10.1053/j.gastro.2012.04.001. Epub 2012 May 15.
3. Serfaty, L., Lemoine, M. Definition and natural history of metabolic steatosis: clinical aspects of NAFLD, NASH and cirrhosis. Diabetes and Metabolism, 2008, 34 (6 Pt 2):634e637.
4. Hepatology. 2012 October; 56(4): 1580-1584. doi: 10.1002/hep.26031
5. Dulai, P S, Singh, S, Patel, J, Soni, M, Prokop, L J, Younossi, Z, et al. Increased risk of mortality by fibrosis stage in nonalcoholic fatty liver disease: systematic review and meta-analysis. Hepatology, 2017, 65(5):1557e1565.
6. Younossi, Z M, Loomba, R, Rinella, ME, Bugianesi, E, Marchesini, G, Neuschwander-Tetri, B A, et al. Current and future therapeutic regimens for non-alcoholic fatty liver disease (NAFLD) and non-alcoholic steatohepatitis (NASH). Hepatology, 2018, 68(1):361e371.
7. Harvey C B, Williams G R. Mechanism of thyroid hormone action. Thyroid, 2002 June; 12(6):441-6.
8. Bookout A L, Jeong Y, Downes M, Yu R T, Evans R M, Mangelsdorf D J. Anatomical profiling of nuclear receptor expression reveals a hierarchical transcriptional network. Cell, 2006, 126:789-799
9. Flamant F, Baxter J D, Forrest D, Refetoff S, Samuels H H, Scanlan T S, Vennstrom B, Samarut J. International union of pharmacology. LIX. The pharmacology and classification of the nuclear receptor superfamily: thyroid hormone receptors. Pharmacol. Rev., 2006, 58:705-711
10. Haning H, Woltering M, Mueller U, Schmidt G, Schmeck C, Voehringer V, Kretschmer A, Pernerstorfer J. Bioorg. Med Chem Lett., 2005 Apr. 1, 15(7): 1835-40. Novel heterocyclic thyromimetics.
11. Hirano T, Kagechika H. Thyromimetics: a review of recent reports and patents (2004-2009). Expert Opin Ther Pat., 2010 February; 20(2):213-28. doi: 10.1517/13543770903567069.
12. Kowalik M A, Columbano A, Perra A. Thyroid Hormones, Thyromimetics and Their Metabolites in the Treatment of Liver Disease. Front Endocrinol (Lausanne), 2018 Jul. 10; 9:382. doi: 10.3389/fendo.2018.00382. eCollection 2018.
13. Erion M D, Cable E E, Ito B R, Jiang H, Fujitaki J M, Finn P D, Zhang B H, Hou J, Boyer S H, van Poelje P D, Linemeyer D L. Targeting thyroid hormone receptor-beta agonists to the liver reduces cholesterol and triglycerides and improves the therapeutic index. Proc Natl Acad Sci USA., 2007 Sep. 25; 104(39):15490-5. Epub 2007 Sep. 18.
14. Hartley M D, Kirkemo L L, Banerji T, Scanlan T S. A Thyroid Hormone-Based Strategy for Correcting the Biochemical Abnormality in X-Linked Adrenoleukodystrophy. Endocrinology 2017, 158(5), p1328-1338. doi: 10.1210/en.2016-1842.
15. Milanesi A, Brent G A. Beam Me In: Thyroid Hormone Analog Targets Alternative Transporter in Mouse Model of X-Linked Adrenoleukodystrophy. Endocrinology 2017, 158, p1116-1119. doi: 10.1210/en.2017-00206.

EMBODIMENTS

Embodiment P1. A method of selectively modulating the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a blood plasma concentration in a rat of about 336 ng/mL at 12 hours after intravenous administration.

Embodiment P2. A method of selectively modulating the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a half-life in a rat of about 5.25 hours after intravenous administration.

Embodiment P3. A method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a blood plasma concentration in a rat of about 336 ng/mL at 12 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P4. A method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a half-life in a rat of about 5.25 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P5. The method of any one of embodiments 1-4, wherein the compound has at least a 9-fold selectivity for thyroid hormone receptor beta over thyroid hormone receptor alpha.

Embodiment P6. The method of any one of embodiments 1-5, wherein the compound has a half-life of over 360 minutes in a mouse, rat, or human hepatocyte assay.

Embodiment P7. The method of any one of embodiments 1-6, wherein the compound is compound 1a.

Additional Embodiments

Embodiment 1. An enantiomeric compound obtained through chromatography purification of a mixture consisting of

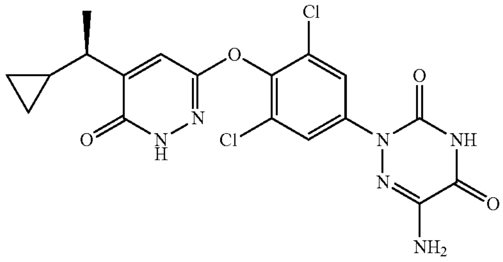 [SMILES: C[C@@H](c1cc(Oc2c(Cl)cc(-n3nc(N)c(=O)[nH]c3=O)cc2Cl)n[nH]c1=O)C1CC1]

and

-continued

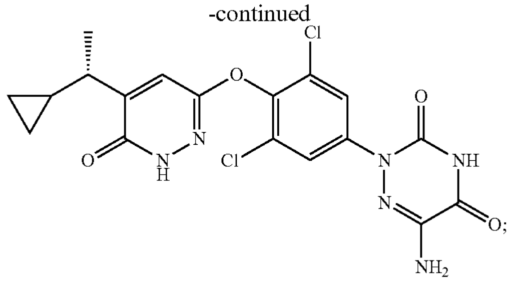

wherein the purification is performed using a 2 cm×25 cm column containing amylose tris-[(S)-α-methylbenzylcarbamate] coated on 5 μm silica gel, under conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm;

and the enantiomeric compound is eluted first under the conditions.

Embodiment 2. The enantiomeric compound of embodiment 1 having greater THR-β activity in a TR-FRET thyroid receptor beta coactivator assay or a HEK293T cell reporter assay than its enantiomeric counterpart which elutes second during the chromatography purification.

Embodiment 3. A compound having a chemical structure of:

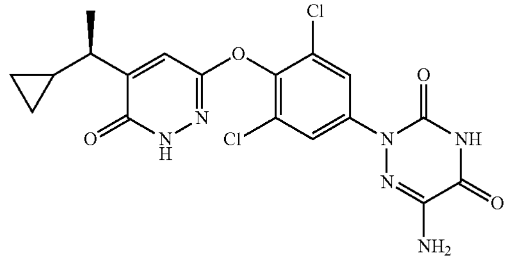

or a pharmaceutically acceptable salt thereof.

Embodiment 4. A compound having a chemical structure of:

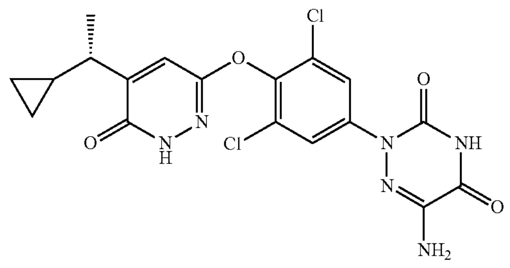 [SMILES: C[C@H](c1cc(Oc2c(Cl)cc(-n3nc(N)c(=O)[nH]c3=O)cc2Cl)n[nH]c1=O)C1CC1]

or a pharmaceutically acceptable salt thereof.

Embodiment 5. A compound that has a retention time of about 20.8 minutes when determined using a 2 cm×25 cm column containing amylose tris-[(S)-α-methylbenzylcarbamate] coated on 5 μm silica gel, under conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm;

wherein the compound is an enantiomer of

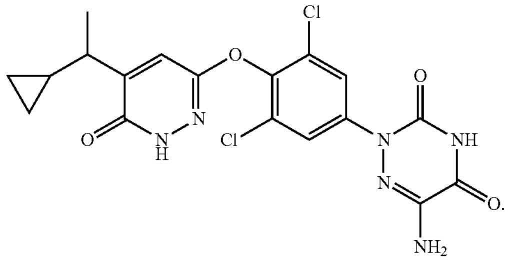 [SMILES: CC(c1cc(Oc2c(Cl)cc(-n3nc(N)c(=O)[nH]c3=O)cc2Cl)n[nH]c1=O)C1CC1]

Embodiment 6. A method of selectively increasing the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a blood plasma concentration in a rat of about 300-400 ng/mL at 12 hours after intravenous administration, wherein the compound is an enantiomer of

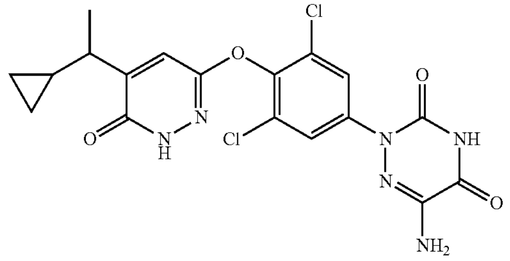

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

Embodiment 7. The method of embodiment 6, wherein the blood plasma concentration is about 336 ng/mL.

Embodiment 8. A method of selectively increasing the activity of a thyroid hormone receptor beta (THR-β) comprising contacting a composition comprising a compound, or a tautomer thereof, or a pharmaceutically acceptable salt thereof, with the thyroid hormone receptor, wherein the composition provides a half-life in a rat of about 5.25 hours after intravenous administration, and wherein the compound is an enantiomer of

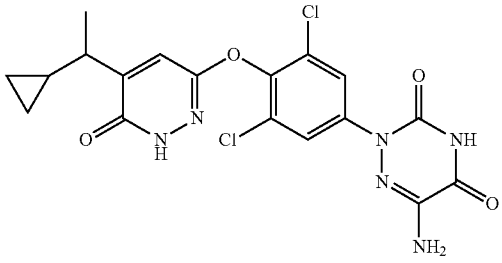

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

Embodiment 9. A method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a blood plasma concentration in a rat of about 300-400 ng/mL at 12 hours after intravenous administration, and wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer, and wherein the compound is an enantiomer of

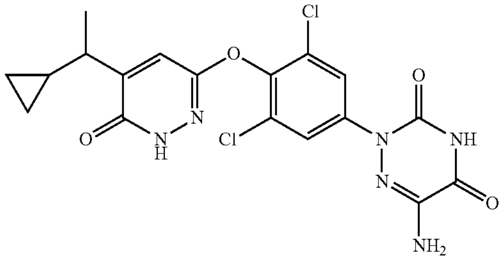

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

Embodiment 10. The method of embodiment 9, wherein the blood plasma concentration is about 336 ng/mL.

Embodiment 11. A method of treating a disorder or disease in a subject in need thereof, the method comprising administering to the subject a therapeutically effective amount of a composition comprising a compound, or a tautomer thereof, or a pharmaceutically acceptable salt thereof, wherein the composition provides a half-life in a rat of about 5.25 hours after intravenous administration, and wherein the disorder or disease is selected from non-alcoholic steatohepatitis (NASH), obesity, hyperlipidemia, hypercholesterolemia, diabetes, liver steatosis, atherosclersis, cardiovascular diseases, hypothyroidism, and thyroid cancer, and wherein the compound is an enantiomer of

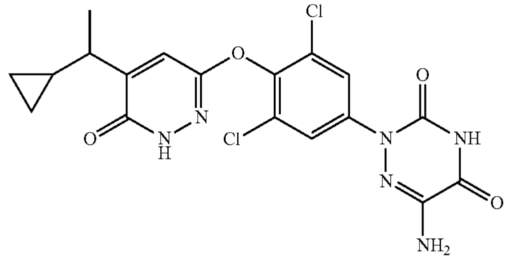

that elutes first when using a 2 cm×25 cm column containing amylose tris-[(S)-α-methylbenzylcarbamate] coated on 5 μm silica gel, under chromatography conditions wherein:

Mobile Phase A: $CO_2$;

Mobile Phase B: $CH_3OH$ (0.1% 2M $NH_3$—$CH_3OH$);

Gradient: 20% B;

Flow Rate: 45 mL/min; and

UV detection: λ=220 nm.

Embodiment 12. The method of any one of embodiments 6-11, wherein the compound has at least a 9-fold selectivity for thyroid hormone receptor beta over thyroid hormone receptor alpha in a TR-FRET thyroid receptor beta coactivator assay.

Embodiment 13. The method of any one of embodiments 6-12, wherein the compound has a half-life of over 360 minutes in a mouse, rat, or human hepatocyte assay.

Embodiment 14. The method of any one of embodiments 6-13, wherein the compound has greater THR-β activity in a TR-FRET thyroid receptor beta coactivator assay than its enantiomeric counterpart which elutes second under the chromatography conditions.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A compound having a chemical structure of:

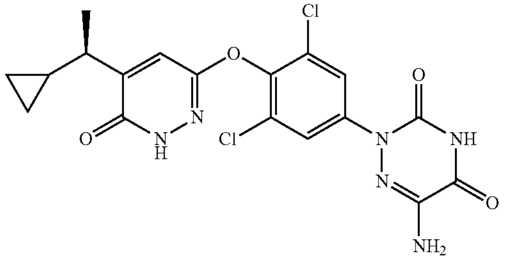

or a pharmaceutically acceptable salt thereof.

2. A compound having a chemical structure of:

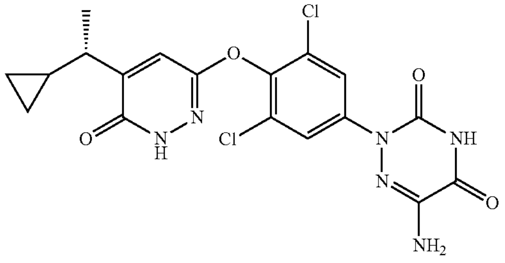 [SMILES: C[C@H](c1cc(Oc2c(Cl)cc(-n3nc(N)c(=O)[nH]c3=O)cc2Cl)n[nH]c1=O)C1CC1]

or a pharmaceutically acceptable salt thereof.

* * * * *